(12) United States Patent
Banyay et al.

(10) Patent No.: US 9,212,898 B2
(45) Date of Patent: Dec. 15, 2015

(54) METHOD AND DEVICE FOR THREE-DIMENSIONAL CONFOCAL MEASUREMENT

(75) Inventors: Matus Banyay, Cologne (DE); Frank Thiel, Ober-Ramstadt (DE)

(73) Assignee: Sirona Dental Systems GMBH, Bensheim (DE)

( * ) Notice: Subject to any disclaimer, the term of this patent is extended or adjusted under 35 U.S.C. 154(b) by 29 days.

(21) Appl. No.: 14/343,495

(22) PCT Filed: Sep. 10, 2012

(86) PCT No.: PCT/EP2012/067619
§ 371 (c)(1),
(2), (4) Date: Jul. 14, 2014

(87) PCT Pub. No.: WO2013/034754
PCT Pub. Date: Mar. 14, 2013

(65) Prior Publication Data
US 2014/0313524 A1  Oct. 23, 2014

(30) Foreign Application Priority Data

Sep. 8, 2011 (DE) .......................... 10 2011 082 349

(51) Int. Cl.
*G01B 11/14* (2006.01)
*G01B 11/02* (2006.01)
(Continued)

(52) U.S. Cl.
CPC .............. *G01B 11/02* (2013.01); *A61C 9/0066* (2013.01); *A61C 19/04* (2013.01); *G01B 11/0608* (2013.01); *G01B 11/2513* (2013.01); *G02B 21/0072* (2013.01); *G02B 27/48* (2013.01)

(58) Field of Classification Search
CPC ........ G01B 11/24; G01B 11/02; G01B 11/14; G03F 7/70625; G01N 21/4788

USPC ........................................................ 356/625
See application file for complete search history.

(56) References Cited

U.S. PATENT DOCUMENTS 5,563,710 A   10/1996  Webb et al.
6,115,111 A    9/2000  Korah et al.
(Continued)

FOREIGN PATENT DOCUMENTS

EP    1371939    12/2003
EP    1505425     8/2008

OTHER PUBLICATIONS

International Search Report dated Dec. 11, 2012; International Application No. PCT/EP2012/067619; International Filing Date: Sep. 10, 2012; 4 pages.
(Continued)

*Primary Examiner* — Tarifur Chowdhury
*Assistant Examiner* — Md Rahman
(74) *Attorney, Agent, or Firm* — Blank Rome LLP

(57) ABSTRACT

The invention relates to a method and a device for three-dimensional measurement of an object. The device includes a laser source for generating an illumination beam, a focusing optics for focusing the illumination beam on at least one measuring point on a surface of the object to be measured, a detector for detecting an observation beam reflected by the surface of the object, a confocal observation optics which allows only the observation beam that is focused on the surface of the object to pass through to the detector. The laser source includes multiple coherent laser elements, the laser elements simultaneously emitting illumination beams that are focused on multiple measuring points on the surface of the object, so that the laser elements are arranged to reduce the speckle effect in the 3D-image data generated by the measurement.

12 Claims, 3 Drawing Sheets

(51) Int. Cl.
*G02B 21/00* (2006.01)
*G02B 27/48* (2006.01)
*G01B 11/06* (2006.01)
*G01B 11/25* (2006.01)
*A61C 9/00* (2006.01)
*A61C 19/04* (2006.01)

(56) References Cited

U.S. PATENT DOCUMENTS 6,121,603 A 9/2000 Hang et al.
6,154,479 A * 11/2000 Yoshikawa et al. ............. 372/96
2004/0147810 A1 7/2004 Mizuno
2008/0019127 A1 1/2008 Dick et al.
2009/0201577 A1* 8/2009 LaPlante et al. ............... 359/355
2012/0075425 A1* 3/2012 Thiel ............................... 348/46

OTHER PUBLICATIONS

Translation of International Search Report; International Application No. PCT/EP2012/067619; 3 pages.

* cited by examiner

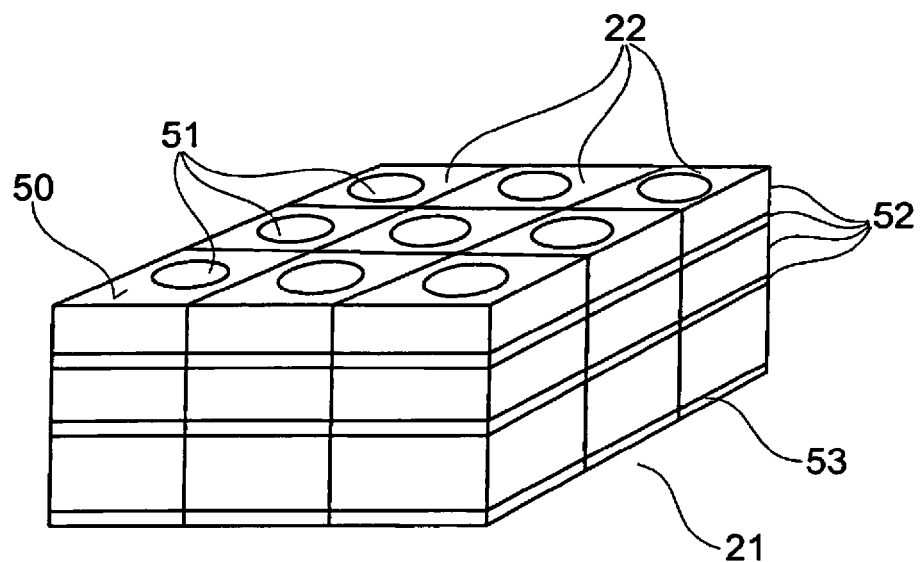
Fig. 4
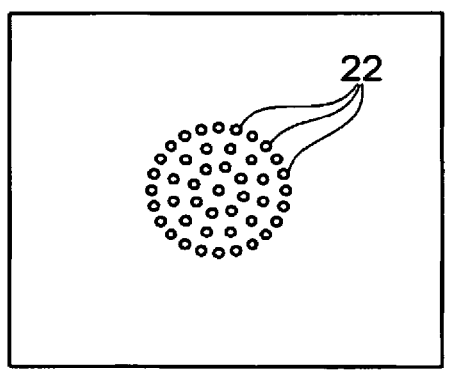 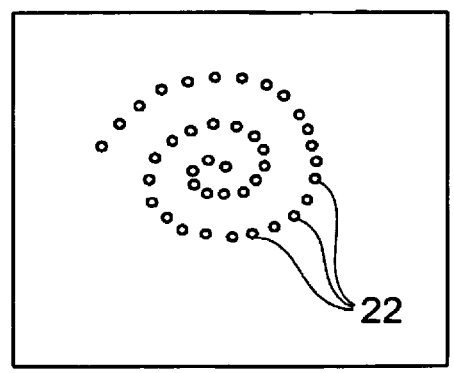
Fig. 5      Fig. 6

METHOD AND DEVICE FOR THREE-DIMENSIONAL CONFOCAL MEASUREMENT

TECHNICAL FIELD

The invention relates to a method and a device for three-dimensional measurement of an object using a confocal microscopy method. This device comprises a laser source for generating an illumination beam, a focusing optics for focusing the illumination beam on at least one measuring point on an object surface to be measured, a detector for detection of an illumination beam reflected back from the object surface and a confocal observation optics which allows only the illumination beam that is focused on the object surface to pass through to the detector.

PRIOR ART

Several methods and devices for confocal measurement which use a laser source are known from the prior art. The use of a laser source is associated with an optical phenomenon known as the speckle effect. This speckle effect is an interference phenomenon observed with sufficiently coherent illumination of uneven object surfaces. The result is a speckle pattern manifested as noise over both time and space. To reduce the speckle effect, the light parameters of the illuminating laser beam such as the angle of incidence, the polarization and the wavelength are usually modified. Optical diffusers or mechanically moving optical elements are therefore used in most cases.

EP 1 505 425 B1 discloses a device for confocal imaging, wherein the imaging lens comprises an optical component which is movable, so that within a range of movement and within the integration time of the detector the focal point on the object is moved to a number of different locations in a plane perpendicular to the optical axis. The location of the focal point is therefore modeled within the integration time of the detector, so that the confocal signal is blurred and the speckle effect is thereby reduced.

U.S. Pat. No. 4,155,630 discloses a method and a device for improving image generation using a coherent measurement system, wherein a mirror is mechanically put into a wobbling motion to thereby modify the angle of incidence of the laser beam.

U.S. Pat. No. 6,081,381 discloses a method and a device for eliminating the speckle effect of an optical system using a diffuser and a rotating microlens array.

U.S. Pat. No. 4,511,220 discloses a device for reducing the speckle effect of a laser system, wherein two polarized laser beams having a known coherence length and not coherent to one another are superimposed, and the speckle effect is thereby minimized.

One disadvantage of the aforementioned method is that to minimize the speckle effect the laser beam must be modified in various ways using various movable optical means. A substantial technical complexity is associated with the activation and integration of these optical means. Furthermore the mechanics for adjusting these optical means are susceptible to malfunction and may lead to an exacerbation of the image quality of the 3D-image data generated by means of the three-dimensional confocal measurement.

The present invention therefore seeks to solve the problem of providing a device for three-dimensional confocal measurement to minimize the speckle effect in a simple manner

PRESENTATION OF THE INVENTION

One subject matter of the invention is a device for three-dimensional measurement of an object using a confocal microscopy method, comprising a laser source for generating an illumination beam, a focusing optics for focusing the illumination beam on at least one measuring point on an object surface to be measured, a detector for detecting an observation beam reflected by the object surface, a confocal observation optics which allows only the observation beam focused on the object surface to pass through to the detector. The laser source comprises multiple coherent laser elements, wherein the laser elements simultaneously emit illumination beams which are focused on multiple measuring points on the object surface, wherein the laser elements are arranged such that the speckle effect in the 3D-image data generated in the measurement is reduced compared to that of a measurement using a device having only a spot laser source.

According to the confocal microscopy method, the illumination beam is focused on a measuring point in a focal plane on the object surface by means of the focusing optics which may comprise a collimator lens. The observation beam is reflected by the object and passes through the focusing optics to the observation optics which comprises an aperture. The observation beam can be deflected to the observation optics by means of a beam splitter. The aperture is in a confocal arrangement with the focal plane so that only the light from the focal plane reaches the detector. The object can be scanned point-for-point to then assemble a three-dimensional image from the measured data by means of a computer. The focal point may be shifted in the direction of an optical axis of the device and orthogonally to said device.

The reflected observation beam means both reflection and scattering at the object surface.

To shorten the measurement time, the device may have multiple confocal channels, wherein each confocal channel has a focusing optics with its own collimator lens and observation optics with its own aperture. For each confocal channel a separate laser source may be used or a shared laser source may be used for all channels. The laser sources may be arranged in a plane on a circuit board. The collimator lens may be arranged in a lens array. The apertures may also be arranged in a plane in an aperture array. Multiple focal points can thereby be projected simultaneously onto the object to measure a plane of the object. The focal points may then be shifted, layer-for-layer, in the direction of the optical axis of the device to completely measure the object. A depth scan is thus performed with each of the confocal channels simultaneously.

The individual laser sources and/or each of the laser sources in a laser source array in turn comprise multiple coherent laser elements. The illumination beams of the laser elements of a laser source are focused on a bundle of measuring points on the object surface. In the case of a laser source array, the illumination beams are focused on multiple bundles of measuring points. The measuring points within the bundle are arranged so close together that they cannot be resolved by means of the observation optics, thereby blurring portions of each of the laser elements. The portions of the observation beams of the laser elements are thus averaged, so that only one measuring point with an average intensity is recorded on the detector. This reduces the speckle effect.

The reduced resolution of the observation optics may be caused, for example, by diffraction of the laser beams on an aperture of the entire observation optics leading to so-called disks, depending on the shape of the aperture. The optical design of the observation optics thus acts as a limiting factor for the resolution. If the aperture is not correctly positioned confocally or if the size of the aperture in the confocal plane is wrong, this can also lead to a reduced resolution of the entire optical system.

One advantage of this device is that the laser elements of the laser source are focused on a bundle of measuring points to reduce the speckle effect, so that no mechanical means are necessary for modification of the laser beam in comparison with the known methods.

Another advantage of the present device is that the device can be designed to be more compact than conventional devices because mechanical means and control thereof are not necessary.

The laser elements can advantageously emit illumination beams, which are modulated in their wavelength and have different wavelengths from one another within a wavelength range.

In this way the wavelengths of the individual laser elements differ from one another so that the speckle effect is additionally diminished by the modulation of the wavelength. The wavelength range is selected to be large enough so that the speckle effect is reduced to the required extent.

The observation beams reflected by the object can advantageously be blurred by diffraction at an aperture of the observation optics so that portions of the observation beams are averaged and the detector detects a shared projection point having an average intensity. The diffraction of the observation beams on an aperture of the observation optics can lead to diffraction disks formed according to the shape and size of a confocally arranged aperture in the observation optics.

The wavelength range within which the wavelength of the laser elements is modulated can advantageously be at most 60 nm.

In this way the interference between the observation beams of the individual laser elements is reduced to an even greater extent and thus leads to a weaker speckle effect.

The wavelengths of the individual laser elements within the wavelength range can advantageously be distributed randomly.

In this way the wavelengths are not distributed according to a certain pattern within the wavelength range, thus making the interference between the observation beams of the laser elements low.

The laser elements can advantageously emit illumination beams of the same wavelength.

In this alternative version of the device, all the laser elements emit laser light of the same wavelength so that the interference between the observation beams of the laser elements and thus the speckle effect are minimized only by the distribution of the measuring points within the bundle range on the object.

The laser elements can advantageously be laser diodes arranged side-by-side on a shared circuit board.

In this way the laser source can have very compact design to minimize the dimensions of the present device, in particular with regard to its use in the dental field.

The laser elements can advantageously be VCSEL elements which are arranged side-by-side on a VCSEL chip.

The VCSEL (vertical cavity surface emitting laser) element is a semiconductor laser, in which the light is emitted at a right angle to the plane of a semiconductor chip. With conventional edge emitters, in contrast, the light with is emitted at one or two flanks of the semiconductor chip. The advantages of using a VCSEL element consist of low manufacturing costs, low power consumption, an improved beam profile compared to edge emitters, the tunability of the wavelength and the high intrinsic modulation bandwidth. Furthermore, VCSEL elements can be manufactured in grid arrangements in a plane.

The laser elements may advantageously be arranged at the same distance from one another along the rows and columns of a two-dimensional orthogonal matrix, in a spiral pattern or in the form of concentric circles.

In this way the laser elements in a laser element array are arranged in the form of an orthogonal matrix which can be produced easily and fully automatically.

The laser elements can advantageously be arranged in a laser element array according to a random distribution.

Interference that may occur due to recurring patterns is thereby reduced.

A plane in which the laser elements are arranged can advantageously be aligned perpendicular to an emission direction of the illumination beams.

The laser elements are thereby arranged in a plane perpendicular to the optical axis of the device, so that the distribution of the measuring points on the object leads to a reduction in interference and thus in the speckle effect.

The laser source can advantageously comprise at least 50 laser elements.

The number of laser elements is therefore sufficient to reduce the speckle effect to the required extent.

The device can advantageously be dimensioned allowing it to be integrated into a conventional dental handpiece and making it suitable for measuring teeth as the object.

The device can therefore be used in the dental field for measuring teeth and other dental objects.

Another subject matter of the invention is a method for three-dimensional measurement of an object using a confocal microscopy method, wherein a laser source emits an illumination beam, wherein the illumination beam is focused on at least one measuring point on an object surface to be measured, wherein an observation beam reflected by the object surface is detected by a detector, wherein an observation optics has an aperture which allows only the observation beam focused on the object surface to pass through to the detector. The laser source comprises multiple coherent laser elements, wherein the laser elements emit illumination beams simultaneously during the measurement, these beams being focused on multiple measuring points on the object surface, and the laser elements being arranged so that the speckle effect in the 3D-image data generated in the measurement is reduced.

One advantage of this method is that the speckle effect is easily minimized without using mechanical means as in a conventional method.

The observation optics therefore cannot resolve the individual measuring points of the laser elements so that only the shared projection point having an average intensity is detected on the detector.

The observation beams reflected by the object may advantageously be blurred by diffraction on an aperture of the observation optics so that portions of the observation beams are averaged and the detector detects a shared projection point with an average intensity. The diffraction of the observation beams on an aperture of the observation optics may lead to diffraction disks, which are formed according to the size and shape of a confocally arranged aperture in the observation optics.

The laser elements can advantageously emit illumination beams which are modulated in their wavelength and have a differing wavelength from one another within a wavelength range.

In this way interference between the observation beams is reduced, and the speckle effect is therefore also reduced in addition to local modulation by the distribution of the laser beams also being reduced by modulation of the wavelength of the individual laser elements.

The wavelengths of the individual laser elements within the wavelength range can advantageously be distributed randomly.

Owing to the random distribution of the wavelength within the wavelength range, the interference between the observation beams is reduced especially effectively.

BRIEF DESCRIPTION OF THE DRAWINGS

Exemplary embodiments of the present invention are illustrated in the drawings, which show FIG. 1 a conventional device for three-dimensional measurement;

FIG. 4 a diagram of the laser source with VCSEL elements;

FIG. 5 an arrangement of the laser elements in the form of concentric circles;

FIG. 6 an arrangement of the laser elements in the form of a spiral.

EXEMPLARY EMBODIMENTS

Figure 1:
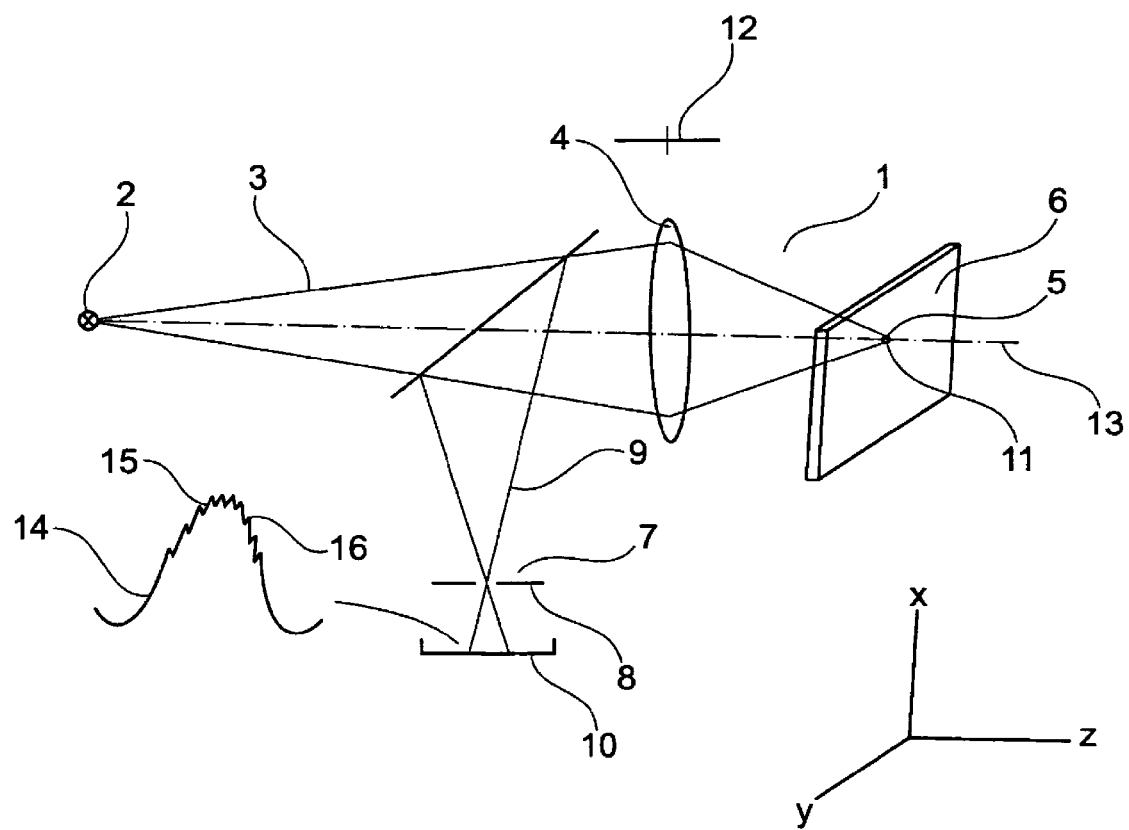

FIG. 1 shows a conventional device 1 known from the prior art for three-dimensional measurement of an object using a confocal microscopy method. The device 1 comprises a simple laser source 2 for generating an illumination beam 3, focusing optics 4 having a collimator lens which focuses the illumination beam 3 on a measuring point 5 on an surface of the object 6 to be measured. The device additionally has observation optics 7 with an aperture 8, which is arranged confocally to the focal plane of the focusing optics 4, so that it allows only an observation beam 9 that has been reflected by the surface of the object 6 back to the detector 10 to pass through. The focal point 11 is shifted by adjusting the focusing optics 4, represented by arrows 12, along an optical axis 13 of device 1 until the focal point 11 strikes the surface of the object 6 and the measuring point 5 can be detected by means of the detector 10. By means of this depth scan the z-coordinate can be determined in the direction of the optical axis. By shifting the focal point 11 along the x-axis and the y axis, the object 6 is then completely measured point-for-point. Three-dimensional image data on the object 6 are calculated by computer from the measured data. Using the conventional device 1 to perform confocal measurement of objects 6 having an irregular surface results in an interference phenomenon known as the speckle effect. In the depth scan for each of the measuring points 5, a depth profile 14 is generated as a function of the z-coordinate. The z-coordinate of the measuring point can then be determined on the surface of the object 6 on the basis of a maximum value 15 of the depth profile. The speckle effect leads to signal noise 16, which increases with intensity and thus falsifies the confocal measurement.

Figure 2:
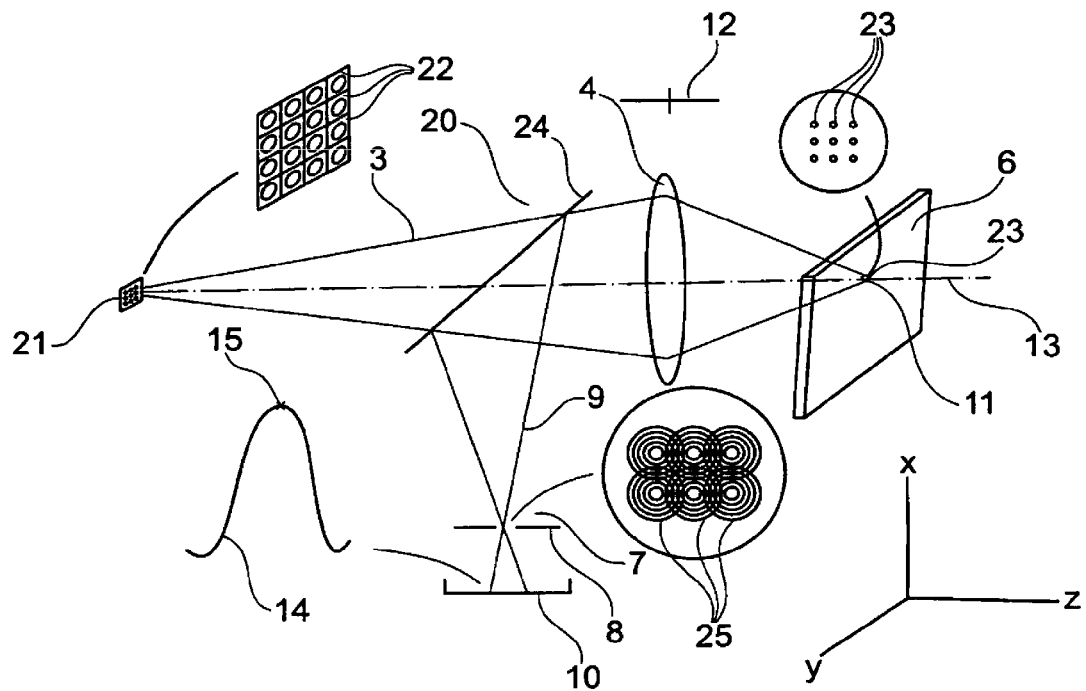
FIG. 2 a device for three-dimensional measurement according to the invention.

FIG. 2 shows a device 20 according to the present invention. In contrast with the conventional device 1 from FIG. 1, the device 20 has a laser source 21 comprised of multiple laser elements 22. In the embodiment shown here, the laser elements 22 are arranged on a circuit board in the form of an orthogonal matrix. The laser elements 22 emit illumination beams 3 at simultaneously, these beams being focused on multiple measuring points 23 on the surface of the object 6. Consequently, the measuring points 23 are also arranged in the form of an orthogonal matrix. The reflected observation beams 9 are deflected by means of a beam splitter 24 to the observation optics with the aperture 8 and then strike the detector 10. Diffraction of the observation beams 9 on an aperture of the entire observation optics causes so-called diffraction disks 25 for each observation beam. The observation optics 7 therefore cannot resolve the individual observation beams 9 of the measuring points 23, so that the portions of the observation beams 9 are blurred and, due to the averaging effect, the detector detects only a single measuring point having the average intensity. This thereby reduces the interference between the observation means and thus also the speckle effect. The depth profile 14 then runs smoothly compared to the depth profile from FIG. 1, so that the maximum point 15 and thus the z-coordinate of the object surface can be determined more accurately.

Figure 3:
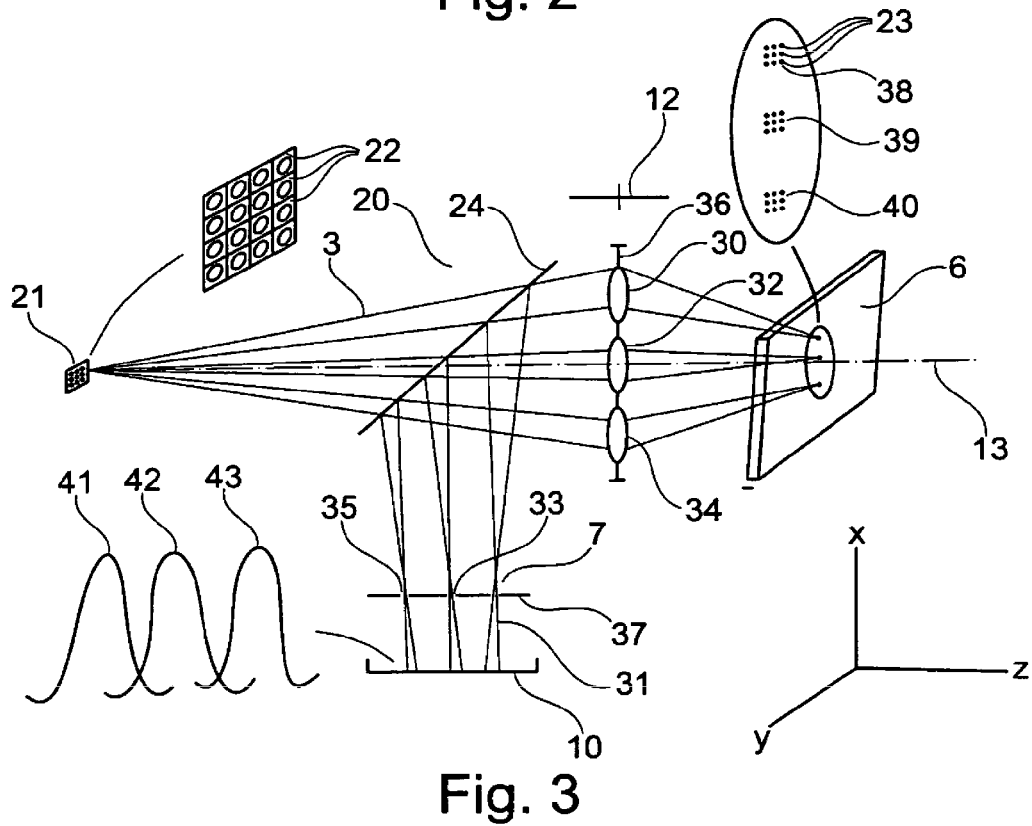
FIG. 3 another embodiment of the device having multiple confocal channels.

FIG. 3 shows another embodiment of the device 20, wherein there are multiple confocal channels compared to the device from FIG. 2. A first confocal channel has a first collimator lens 30 and a first aperture 31. A second confocal channel has a second collimator lens 32 and a second aperture 33. The third confocal channel has a third collimator 34 and a third aperture 35. The three confocal channels use the illumination beams 3 of the shared laser source 21. Alternatively, each confocal channel can have its own laser source. The collimator lenses are arranged in a lens array 36 in a plane. The apertures 31, 33 and 35 are arranged in an aperture array 37 in a plane. Owing to the optical structure shown here, a first bundle 38 of measuring points 23 of the first confocal channel, a second bundle 39 and a third bundle 40 are projected onto the surface of the object 6. In this way three depths scans can be performed simultaneously to ascertain three z-coordinates of the object 6. When there are multiple confocal channels, for example, in the case of a matrix of 100×100 channels, the object 6 can be measured completely layer-by-layer. The duration of the measurement is thereby shortened because scanning of the object 6 along the x-axis and the y axis is omitted. The depth scan with the first channel yields a first depth profile 41. The depth scan with the second channel yields a second depth profile 42. The depth scan with the third channel yields a third depth profile 43.

FIG. 4 shows a diagram of the laser source 21 from FIG. 2 and FIG. 3, where the laser elements 22 are VCSEL elements which are arranged side-by-side on a chip. Each VCSEL element is a semiconductor laser in which the laser light is emitted perpendicularly to a plane 50. The light-generating elements 51 are illustrated in the form of circles. The VCSEL elements are arranged in the form of an orthogonal matrix. The VCSEL elements are constructed from multiple semiconductor layers 52 and have an electric contact 53 on the underside, thus facilitating direct contacting.

FIG. 5 shows a diagram of an arrangement of the laser elements 22 in the form of concentric circles. As an alternative to this, FIG. 6 shows a diagram of an arrangement of the laser elements 22 in the form of a spiral.

LIST OF REFERENCE NUMBERS

1 Conventional device
2 Laser source
3 Illumination beam
4 Focusing optics
5 Measuring point
6 Object
7 Observation optics
8 Aperture
9 Observation beam
10 Detector
11 Focal point
12 Arrows 13 Optical axis
14 Depth profile
15 Maximum value
16 Signal noise
20 Device according to the invention
21 Laser source
22 Laser elements
23 Measuring points
24 Beam splitter
25 Diffraction disk
30 First collimator lens
31 First aperture
32 Second collimator lens
33 Second aperture
34 Third collimator lens
35 Third aperture
36 Lens array
37 Aperture array
38 First bundle
39 Second bundle
40 Third bundle
41 First depth profile
42 Second depth profile
43 Third depth profile
50 Plane
51 Light-generating elements
52 Semiconductor layers
53 Electric contacts

The invention claimed is:

1. A device (20) for three-dimensional measurement of an object (6) using a confocal microscopy method, comprising:
    a laser source (21) for generating an illumination beam (3),
    a focusing optics (4) for focusing the illumination beam (3) on at least one measuring point (5, 23) on a surface of an object (6) to be measured,
    a detector (10) for detecting an observation beam (9) reflected by the surface of the object (6), and
    a confocal observation optics (7) which allows only the observation beam (9) which is focused on the surface of the object (6) to pass through to the detector (10),
    wherein the laser source (21) comprises multiple coherent laser elements (22), the laser elements (22) simultaneously emitting illumination beams (3) which are focused on multiple measuring points (5, 23) on the surface of the object (6), the laser elements (22) being arranged such that the speckle effect in the 3D-image data generated by the measurement is reduced,
    wherein the observation beams (9) reflected by the object (6) are blurred by diffraction on an aperture of the observation optics (7) so that portions of the observation beams (9) are averaged and the detector (10) detects a shared projection point having an average intensity,
    further wherein the diffraction of the observation beams (9) at the aperture of the observation optics (7) leads to diffraction disks (25) which are designed according to the shape and size of a confocally arranged aperture (8) in the observation optics (7).

2. The device (20) according to claim 1, wherein the laser elements (22) emit illumination beams (3) which are modulated in their wavelengths and have a mutually differing wavelength within a wavelength range.

3. The device (20) according to claim 2, wherein the wavelength range within which the wavelength of the laser elements (22) is modulated at most 60 nm.

4. The device (20) according to claim 2, wherein the wavelengths of the individual laser elements (22) are randomly distributed within the wavelength range.

5. The device (20) according to claim 1, wherein the laser elements (22) emit illumination beams (3) of the same wavelength.

6. The device (20) according to claim 1, wherein the laser elements (22) are arranged at the same distance from one another along the rows and columns of a two-dimensional orthogonal matrix in a spiral or in the form of concentric circles.

7. The device (20) according to claim 1, wherein a plane in which the laser elements (22) are arranged is aligned perpendicularly to an emission direction of the illumination beams (3).

8. The device (20) according to claim 1, wherein the laser source (21) comprises at least 50 laser elements (22).

9. The device (20) according to claim 1, wherein the device (20) is designed in its dimensions so that it can be integrated into a traditional dental handpiece and is suitable for measuring teeth as the object (6).

10. A method for three-dimensional measurement of an object (6), comprising the step of using a confocal microscopy, wherein a laser source (21) emits an illumination beam (3), wherein the illumination beam (3) is focused on at least one measuring point (5, 23) on a surface of an object (6) to be measured, wherein an observation beam (9) reflected by the surface of an object (6) is detected by means of a detector (10), wherein an observation optics (7) has an aperture, which allows only the observation beam (9) focused on the surface of the object (6) to pass through to the detector (10), wherein the laser source (21) comprises a plurality of coherent laser elements (22), wherein the laser elements (22) simultaneously emit illumination beams (3) focused on multiple measuring points (5, 23) on the surface of the object (6), wherein the laser elements (22) are arranged to reduce the speckle effect in the 3D-image data generated in the measurement, wherein the observation beams (9) reflected by the object (6) are blurred by diffraction on an aperture of the observation optics (7) so that portions of the observation beams (9) are averaged and the detector (10) detects a shared point having an average intensity, wherein the diffraction of the observation beams (9) on the aperture of the observation optics (7) leads to diffraction disks (25) which are designed according to the shape and size of a confocally arranged aperture (8) in the observation optics (7).

11. The method according to claim 10, wherein the laser elements (22) emit illumination beams (3), which are modulated in their wavelength and have mutually differing wavelengths within a wavelength range.

12. The method according to claim 11, wherein the wavelengths of the individual laser elements (22) within the wavelength range are randomly distributed.

* * * * *